United States Patent
Kaib et al.

(10) Patent No.: US 9,782,578 B2
(45) Date of Patent: Oct. 10, 2017

(54) PATIENT-WORN ENERGY DELIVERY APPARATUS AND TECHNIQUES FOR SIZING SAME

(75) Inventors: Thomas E. Kaib, North Huntingdon, PA (US); Emil Oskin, Natrona Heights, PA (US); Philip C. Skalos, Munhall, PA (US); Jason T. Whiting, Gibsonia, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 0 days.

(21) Appl. No.: 13/460,250

(22) Filed: Apr. 30, 2012

(65) Prior Publication Data

US 2012/0283794 A1 Nov. 8, 2012

Related U.S. Application Data

(60) Provisional application No. 61/481,560, filed on May 2, 2011.

(51) Int. Cl.
*A61N 1/39* (2006.01)
*A61N 1/04* (2006.01)

(52) U.S. Cl.
CPC ......... *A61N 1/0484* (2013.01); *A61N 1/3968* (2013.01); *A61N 1/046* (2013.01)

(58) Field of Classification Search
CPC .... A61N 1/0484; A61N 1/046; A61N 1/3968; A61N 1/39
USPC ................... 607/4, 5; 600/388–390
See application file for complete search history.

(56) References Cited

U.S. PATENT DOCUMENTS

| | | | |
|---|---|---|---|
| 4,094,310 A | | 6/1978 | McEachern et al. |
| 4,432,368 A | * | 2/1984 | Russek .................... A61N 1/22 600/382 |
| 4,632,122 A | | 12/1986 | Johansson et al. |
| 4,698,848 A | * | 10/1987 | Buckley ............................. 2/114 |
| 4,928,690 A | | 5/1990 | Heilman et al. |

(Continued)

FOREIGN PATENT DOCUMENTS

| | | |
|---|---|---|
| EP | 0295497 B1 | 9/1993 |
| EP | 0335356 B1 | 3/1996 |

(Continued)

OTHER PUBLICATIONS

American Journal of Respiratory and Critical Care Medicine, vol. 166, pp. 111-117 (2002). American Thoracic Society, ATS Statement Guidelines for the Six-Minute Walk Test, available at http://ajrccm.atsjournals.org/cgi/content/full/166/1/111.

(Continued)

*Primary Examiner* — George Evanisko
(74) *Attorney, Agent, or Firm* — Lando & Anastasi, LLP

(57) ABSTRACT

A support garment for a patient-worn energy delivery apparatus. A vest-type garment holds an electrode belt in contact with a wearer's ribcage. A removable electrode harness may be attachable to the support garment to accurately position sensing electrodes on the body of the wearer and energy delivery electrodes for transfer of an electrode therapy pulse to the wearer of the garment. The chest garment includes adjustable shoulder straps and a band to accommodate any body size or shape. One-sided assembly and coding of components facilitates use by a patient. A technique for sizing the support garment is also disclosed.

26 Claims, 14 Drawing Sheets

(56) References Cited

U.S. PATENT DOCUMENTS

| | | | |
|---|---|---|---|
| 4,978,926 A | 12/1990 | Zerod et al. | |
| 5,062,834 A | 11/1991 | Gross et al. | |
| 5,078,134 A | 1/1992 | Heilman et al. | |
| 5,348,008 A | 9/1994 | Bornn et al. | |
| 5,353,793 A * | 10/1994 | Bornn | 600/386 |
| 5,365,932 A | 11/1994 | Greenhut | |
| 5,472,453 A | 12/1995 | Alt | |
| 5,564,429 A | 10/1996 | Bornn et al. | |
| 5,662,689 A | 9/1997 | Elsberry et al. | |
| 5,718,242 A | 2/1998 | McClure et al. | |
| 5,738,102 A | 4/1998 | Lemelson | |
| 5,741,306 A | 4/1998 | Glegyak et al. | |
| 5,758,443 A | 6/1998 | Pedrazzini | |
| 5,792,190 A | 8/1998 | Olson et al. | |
| 5,929,601 A | 7/1999 | Kaib et al. | |
| 5,944,669 A | 8/1999 | Kaib | |
| 6,016,445 A | 1/2000 | Baura | |
| 6,065,154 A * | 5/2000 | Hulings | A61N 1/0484 2/102 |
| 6,097,982 A | 8/2000 | Glegyak et al. | |
| 6,097,987 A | 8/2000 | Milani | |
| 6,169,397 B1 | 1/2001 | Steinbach et al. | |
| 6,253,099 B1 | 6/2001 | Oskin et al. | |
| 6,280,461 B1 | 8/2001 | Glegyak et al. | |
| 6,390,996 B1 | 5/2002 | Halperin et al. | |
| 6,681,003 B2 | 1/2004 | Linder et al. | |
| 6,690,969 B2 | 2/2004 | Bystrom et al. | |
| 6,804,554 B2 | 10/2004 | Ujhelyi et al. | |
| 6,827,695 B2 | 12/2004 | Palazzolo et al. | |
| 6,908,437 B2 | 6/2005 | Bardy | |
| 6,990,373 B2 | 1/2006 | Jayne et al. | |
| 7,149,579 B1 | 12/2006 | Koh et al. | |
| 7,220,235 B2 | 5/2007 | Geheb et al. | |
| 7,340,296 B2 | 3/2008 | Stahmann et al. | |
| 7,453,354 B2 | 11/2008 | Reiter et al. | |
| 7,488,293 B2 | 2/2009 | Marcovecchio et al. | |
| 7,810,172 B2 * | 10/2010 | Williams | 2/114 |
| 7,831,303 B2 | 11/2010 | Rueter et al. | |
| 7,974,689 B2 | 7/2011 | Volpe et al. | |
| 8,121,683 B2 | 2/2012 | Bucher et al. | |
| 8,140,154 B2 | 3/2012 | Donnelly et al. | |
| 8,271,082 B2 | 9/2012 | Donnelly et al. | |
| 2003/0004547 A1 | 1/2003 | Owen et al. | |
| 2003/0095648 A1 | 5/2003 | Kaib et al. | |
| 2003/0149462 A1 | 8/2003 | White et al. | |
| 2003/0158593 A1 * | 8/2003 | Heilman et al. | 607/149 |
| 2003/0174049 A1 | 9/2003 | Beigel et al. | |
| 2003/0195567 A1 | 10/2003 | Jayne et al. | |
| 2003/0212311 A1 | 11/2003 | Nova et al. | |
| 2005/0049515 A1 | 3/2005 | Misczynski et al. | |
| 2005/0131465 A1 | 6/2005 | Freeman et al. | |
| 2006/0036292 A1 | 2/2006 | Smith et al. | |
| 2006/0085049 A1 | 4/2006 | Cory et al. | |
| 2006/0178706 A1 | 8/2006 | Lisogurski et al. | |
| 2006/0270952 A1 | 11/2006 | Freeman et al. | |
| 2007/0118056 A1 | 5/2007 | Wang et al. | |
| 2007/0129769 A1 | 6/2007 | Bourget et al. | |
| 2007/0161913 A1 | 7/2007 | Farrell et al. | |
| 2007/0169364 A1 | 7/2007 | Townsend et al. | |
| 2007/0239220 A1 | 10/2007 | Greenhut et al. | |
| 2007/0265671 A1 | 11/2007 | Roberts et al. | |
| 2007/0299474 A1 | 12/2007 | Brink | |
| 2008/0004536 A1 | 1/2008 | Baxi et al. | |
| 2008/0015454 A1 | 1/2008 | Gal | |
| 2008/0030656 A1 | 2/2008 | Watson et al. | |
| 2008/0033495 A1 | 2/2008 | Kumar | |
| 2008/0045815 A1 | 2/2008 | Derchak et al. | |
| 2008/0046015 A1 | 2/2008 | Freeman et al. | |
| 2008/0058884 A1 | 3/2008 | Matos | |
| 2008/0249591 A1 | 10/2008 | Gaw et al. | |
| 2008/0287770 A1 | 11/2008 | Kurzweil et al. | |
| 2008/0306560 A1 | 12/2008 | Macho et al. | |
| 2008/0306562 A1 | 12/2008 | Donnelly et al. | |
| 2008/0312520 A1 * | 12/2008 | Rowlandson et al. | 600/372 |
| 2008/0312709 A1 | 12/2008 | Volpe et al. | |
| 2009/0073991 A1 | 3/2009 | Landrum et al. | |
| 2009/0076336 A1 | 3/2009 | Mazar et al. | |
| 2009/0076340 A1 | 3/2009 | Libbus et al. | |
| 2009/0076341 A1 | 3/2009 | James et al. | |
| 2009/0076342 A1 | 3/2009 | Amurthur et al. | |
| 2009/0076343 A1 | 3/2009 | James et al. | |
| 2009/0076344 A1 | 3/2009 | Libbus et al. | |
| 2009/0076345 A1 | 3/2009 | Manicka et al. | |
| 2009/0076346 A1 | 3/2009 | James et al. | |
| 2009/0076348 A1 | 3/2009 | Manicka et al. | |
| 2009/0076349 A1 | 3/2009 | Libbus et al. | |
| 2009/0076350 A1 | 3/2009 | Bly et al. | |
| 2009/0076363 A1 | 3/2009 | Bly et al. | |
| 2009/0076364 A1 | 3/2009 | Libbus et al. | |
| 2009/0076397 A1 | 3/2009 | Libbus et al. | |
| 2009/0076405 A1 | 3/2009 | Amurthur et al. | |
| 2009/0076410 A1 | 3/2009 | Libbus et al. | |
| 2009/0076559 A1 | 3/2009 | Libbus et al. | |
| 2009/0093687 A1 | 4/2009 | Telfort et al. | |
| 2009/0138059 A1 | 5/2009 | Ouwerkerk | |
| 2009/0234410 A1 | 9/2009 | Libbus et al. | |
| 2009/0264792 A1 | 10/2009 | Mazar | |
| 2009/0275848 A1 | 11/2009 | Brockway et al. | |
| 2009/0287120 A1 | 11/2009 | Ferren et al. | |
| 2009/0292194 A1 | 11/2009 | Libbus et al. | |
| 2010/0056881 A1 | 3/2010 | Libbus et al. | |
| 2010/0069735 A1 | 3/2010 | Berkner | |
| 2010/0076513 A1 | 3/2010 | Warren et al. | |
| 2010/0234715 A1 * | 9/2010 | Shin et al. | 600/388 |
| 2010/0234716 A1 | 9/2010 | Engel | |
| 2010/0298899 A1 | 11/2010 | Donnelly et al. | |
| 2011/0077728 A1 * | 3/2011 | Li | A61H 39/002 607/152 |
| 2011/0196220 A1 * | 8/2011 | Storm | 600/393 |
| 2011/0288604 A1 | 11/2011 | Kaib et al. | |
| 2011/0288605 A1 | 11/2011 | Kaib et al. | |
| 2012/0011382 A1 | 1/2012 | Volpe et al. | |
| 2012/0112903 A1 | 5/2012 | Kaib et al. | |
| 2012/0144551 A1 * | 6/2012 | Guldalian | A61B 5/04085 2/102 |
| 2012/0146797 A1 | 6/2012 | Oskin et al. | |
| 2012/0150008 A1 | 6/2012 | Kaib et al. | |
| 2012/0158074 A1 * | 6/2012 | Hall | 607/5 |
| 2012/0158075 A1 | 6/2012 | Kaib et al. | |
| 2014/0371806 A1 | 12/2014 | Raymond et al. | |
| 2015/0217121 A1 | 8/2015 | Subramanian et al. | |

FOREIGN PATENT DOCUMENTS

| | | |
|---|---|---|
| EP | 1455640 B1 | 1/2008 |
| EP | 1720446 B1 | 7/2010 |
| JP | S6368135 A | 3/1988 |
| JP | 5115450 A | 5/1993 |
| JP | H07541 A | 1/1995 |
| JP | 2002534231 A | 10/2002 |
| JP | 2003233997 A | 8/2003 |
| JP | 2009510276 A | 3/2009 |
| JP | 2009518057 A | 5/2009 |
| WO | 0002484 A1 | 1/2000 |
| WO | 2004054656 A1 | 7/2004 |
| WO | 2006050235 A1 | 5/2006 |
| WO | 2007077997 A1 | 7/2007 |

OTHER PUBLICATIONS

DeBock et al., "Captopril treatment of chronic heart failure in the very old," J. Gerontol. (1994) 49: M148-M152.

O'Keeffe et al., "Reproducability and responsiveness of quality of the assessment and six minute walk test in elderly heart failure patients," Heart (1998) 80: 377-382.

Extended European search report from corresponding European Patent Application Serial No. 12779417.0, mailed Sep. 1, 2014.

Office Action from corresponding European Application No. 12779417.0 dated Nov. 8, 2016.

(56) References Cited

OTHER PUBLICATIONS

Office Action from corresponding Japanese Application No. 2014-509341 dated Nov. 22, 2016.

* cited by examiner

PATIENT-WORN ENERGY DELIVERY APPARATUS AND TECHNIQUES FOR SIZING SAME

CROSS-REFERENCE TO RELATED APPLICATION

This application claims priority under 35 U.S.C. §119(e) to U.S. Provisional Patent Application Ser. No. 61/481,560 filed on May 2, 2011, titled "PATIENT-WORN ENERGY DELIVERY APPARATUS AND TECHNIQUES FOR SIZING SAME" the entire disclosure of which is hereby incorporated herein by reference in its entirety for all purposes.

FIELD OF THE TECHNOLOGY

One or more aspects relate generally to a wearable cardioverter-defibrillator device, and more particularly, to support garments for housing the device and its associated sensing and energy delivery electrodes.

BACKGROUND

Technology is available for correcting excessively slow heart rates (bradycardia) using implantable devices, commonly referred to as pacemakers, which deliver microjoule electrical pulses to a slowly beating heart in order to speed the heart rate up to an acceptable level. Also, it is well known to deliver high energy shocks (e.g., 180 to 360 joules) via external paddles applied to the chest wall in order to correct excessively fast heart rates, and prevent the possible fatal outcome of ventricular fibrillation or certain ventricular tachycardias. Bradycardia, ventricular fibrillation, and ventricular tachycardia are all electrical malfunctions (arrhythmias) of the heart. Each may lead to death within minutes unless corrected by the appropriate electrical stimulation.

One of the most deadly forms of heart arrhythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death may result in minutes if normal heart contractions are not restored.

Because time delays in applying the corrective electrical treatment may result in death, implantable pacemakers and defibrillators have significantly improved the ability to treat these otherwise life threatening conditions. Being implanted within the patient, the device continuously monitors the patient's heart for treatable arrhythmias and when such is detected, the device applies corrective electrical pulses directly to the heart.

Pacemakers and defibrillators that apply corrective electrical pulses externally to the patient's chest wall may be used to correct such life-threatening arrhythmias but suffer from a drawback insofar as it may not be possible to apply the device in time during an acute arrhythmic emergency to save the patient's life. Such treatment is needed within a few minutes to be effective, and the chance of survival begins to diminish rapidly after one minute.

Consequently, when a patient is deemed at high risk of death from such arrhythmias, electrical devices often are implanted so as to be readily available when treatment is needed. Alternatively, such patients are kept in a hospital where corrective electrical therapy is generally close at hand. Long term hospitalization, however, is frequently impractical due to its high cost, or due to the need for patients to engage in normal daily activities.

There also are many patients susceptible to heart arrhythmias who are at temporary risk of sudden death. For example, patients who have suffered a myocardial infarction and have low ejection fraction are at substantial risk of tachyarrhythmias for several weeks thereafter. Such patients generally are hospitalized but could be discharged earlier if there were a practical means to protect them from life threatening arrhythmias. Additionally, patients awaiting implantation of an automatic defibrillator may require an external defibrillator to be close at hand, in case they experience a life-threatening tachyarrhythmia. Furthermore, some patients who may benefit from an implantable defibrillator may face an inordinate risk from the surgery required for implanting such a device.

Wearable external defibrillators are known, such as those disclosed in U.S. Pat. No. 5,741,306 assigned to the assignee hereof and hereby incorporated herein by reference in its entirety for all purposes. A wearable defibrillator may provide a patient-worn energy delivery apparatus for imparting electrical therapy to the body of a patient responsive to detection of a treatable condition. An important consideration in the proper operation of the device is accurate sensing of the treatable condition by the apparatus and delivery of the electrical energy to the person's body by electrodes. The electrodes must be placed on the person's body in the correct position in order to effectively perform these functions. It is typically desirable that the electrodes be positioned on both the front and back of the patient in order to provide the most effective electrical therapeutic pulse to the body. Additionally, since the wearable defibrillator is designed to be worn by the patient over extended periods of time, the use of skin-irritating substances commonly used on a more temporary basis to attach electrodes to a patient is typically avoided.

SUMMARY

Aspects relate generally to a wearable apparatus for supporting a defibrillator while accurately positioning the wearable defibrillator electrodes on a patient's body, even during typical body motion, and most especially during motion which may occur when the patient is experiencing an arrhythmic episode.

One or more aspects may generally be directed to alleviating any reluctance of patients to regularly change and launder defibrillator support garments due to a perception that the assembly and disassembly process is too complicated. Comfort, proper fit, sanitation, and accurate electrode placement may be promoted.

Aspects may provide support garments for a patient-worn energy delivery apparatus. The garment may hold a defibrillator device and its associated sensing and energy delivery electrodes. The garment may include a vest-like chest garment including elements to provide support for the defibrillator electrodes and other associated components. Other elements of the chest garment may be directed to accurately positioning sensing electrodes and energy delivery electrodes on a patient's body. In some aspects, the chest garment may include adjustable shoulder straps and an adjustable belt so the support garment can accommodate any body size or shape. Certain aspects are directed to facilitating assembly and disassembly of the garment system by a patient. In at least some embodiments, one-sided assembly is enabled. Techniques for properly sizing the garment are also disclosed.

In accordance with one or more aspects, a patient-worn energy delivery system may comprise a defibrillator device, a support garment constructed and arranged to support the defibrillator device, the support garment configured to be worn by a patient and constructed and arranged for one-sided assembly, the support garment further comprising a belt and adjustable shoulder straps configured to be selectively attached to the belt; and a coding system configured to facilitate attachment of the defibrillator device to the support garment.

In some embodiments, the shoulder straps may be selectively attached to the belt at a front of the patient. In at least one embodiment, the support garment comprises an elastic, low spring rate material.

In accordance with one or more embodiments, a patient measuring band may comprise a plurality of coded zones along a length of the measuring band, each coded zone corresponding to a defibrillator support garment size based on a patient body circumference.

In accordance with one or more embodiments, a method of fitting a defibrillator support garment to a patient may comprise extending a patient measuring band around a chest of a patient, the measuring band comprising a plurality of coded zones along a length of the measuring band, each coded zone corresponding to a defibrillator support garment size based on a patient body circumference, selecting a defibrillator support garment based on the defibrillator support garment size identified by the patient measuring band, applying a defibrillator device in the defibrillator support garment based on a coding system configured to facilitate attachment of the defibrillator device to the defibrillator support garment, preparing the defibrillator support garment for wear by the patient with a one-side assembly process, and securing the defibrillator support garment to the patient.

In some embodiments, securing the defibrillator support garment to the patient involves securing shoulder straps of the defibrillator support garment to a band of the defibrillator support garment at a front of the patient.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

Various aspects of at least one embodiment are discussed below with reference to the accompanying figures. The figures are provided for the purposes of illustration and explanation and are not intended as a definition of the limits of the invention. In the figures.

DETAILED DESCRIPTION

In accordance with one or more embodiments, a cardioverter defibrillator may be worn by a patient at risk for sudden cardiac arrest (SCA). The defibrillator may monitor the patient's heart continuously and, if the patient goes into a life-threatening arrhythmia, can deliver a shock treatment to restore the patient's heart to a normal rhythm.

Figure 1:
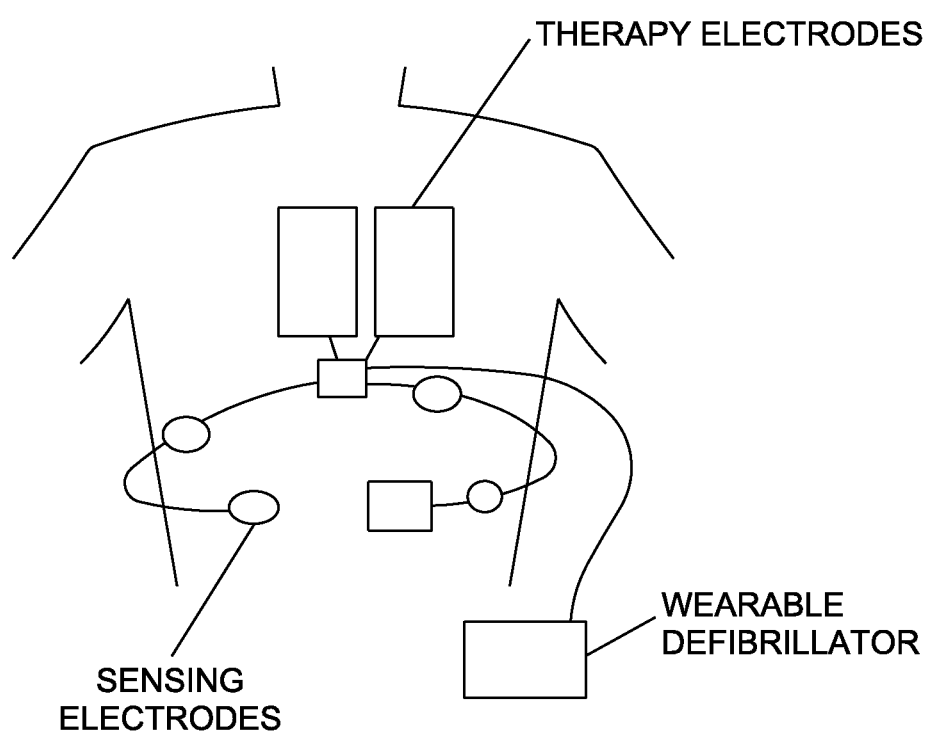
FIG. 1 presents a schematic of a patient-worn energy delivery apparatus in accordance with one or more embodiments.
Figure 2A:
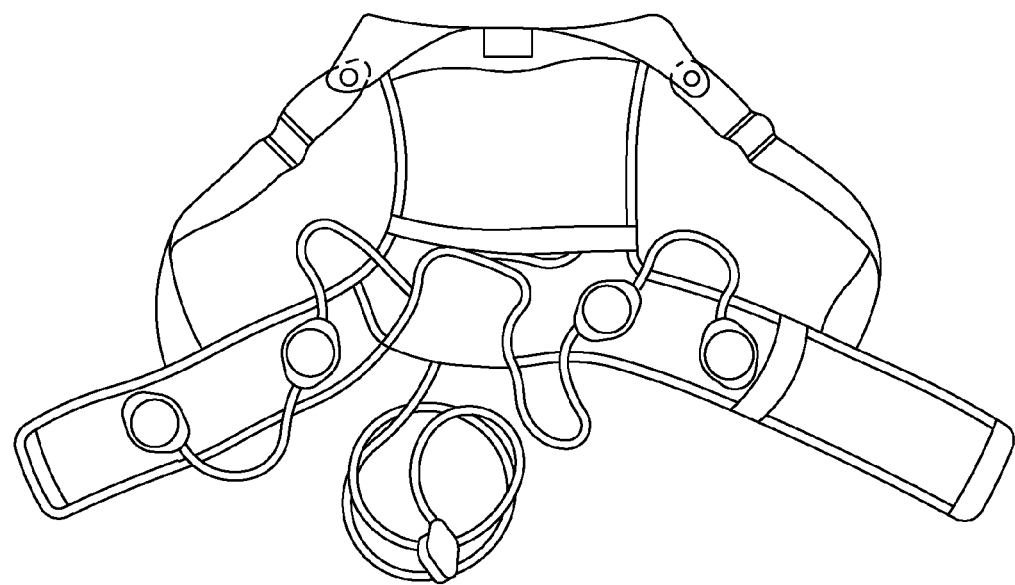
FIGS. 2A and 2B present schematics (front and back views, respectively) of a defibrillator support garment in accordance with one or more embodiments.
Figure 2B:
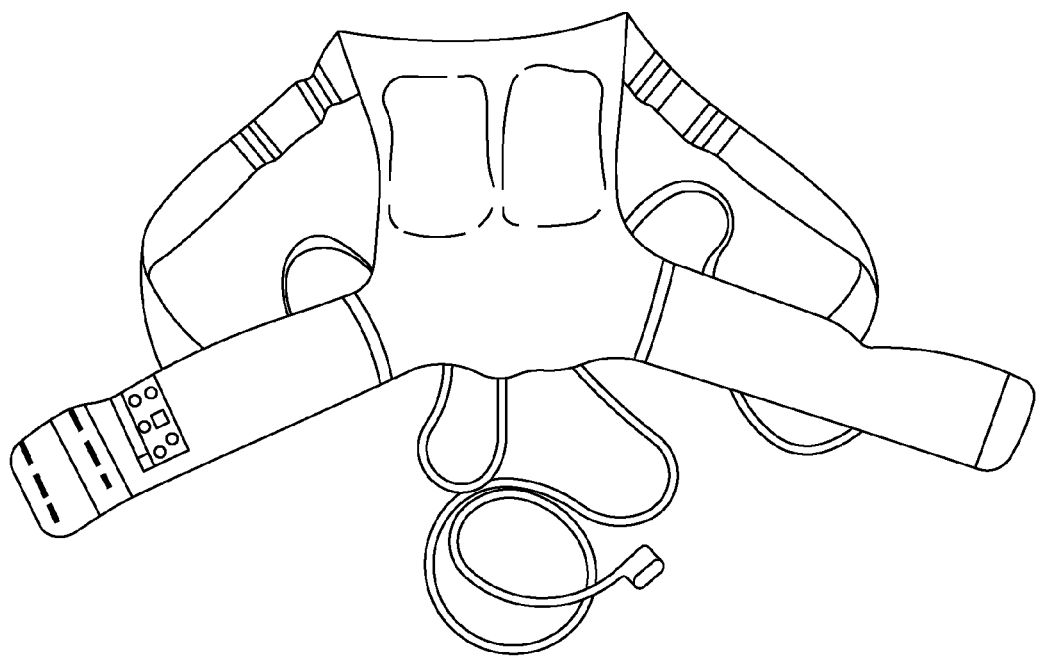
Figure 3A:
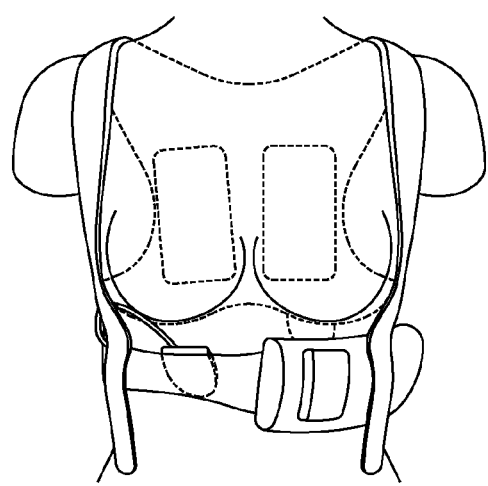
FIGS. 3A and 3B present front and back views, respectively, of shoulder straps in accordance with one or more embodiments.
Figure 3B:
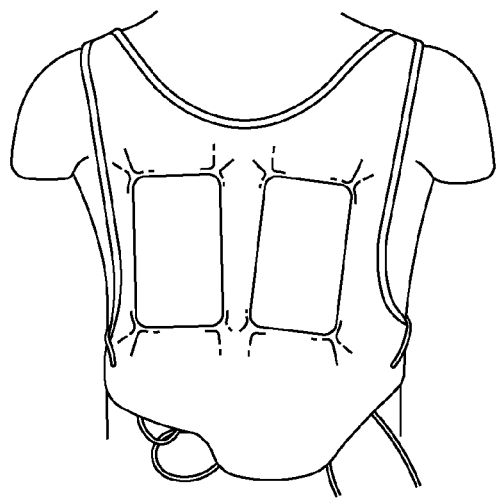
Figure 4A:
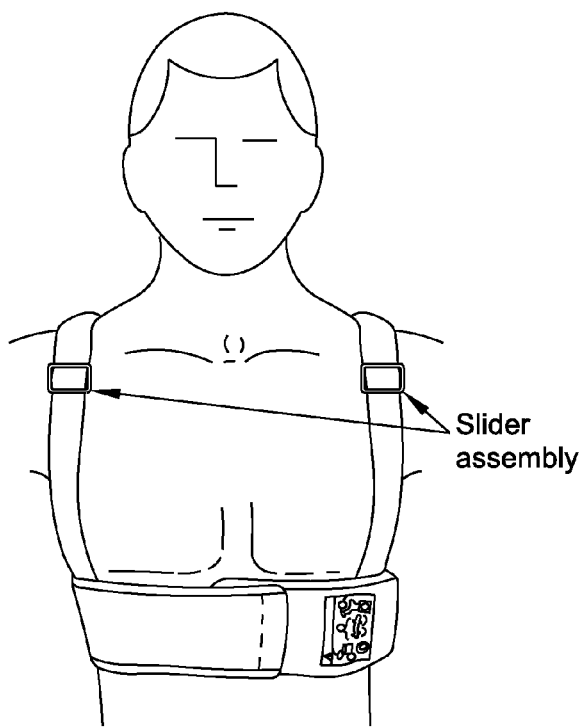
FIGS. 4A and 4B present front and back views, respectively, of shoulder straps in accordance with one or more embodiments.
Figure 4B:
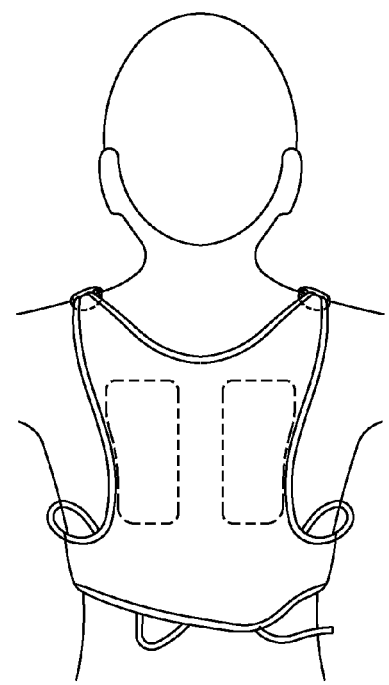
Figure 5A:
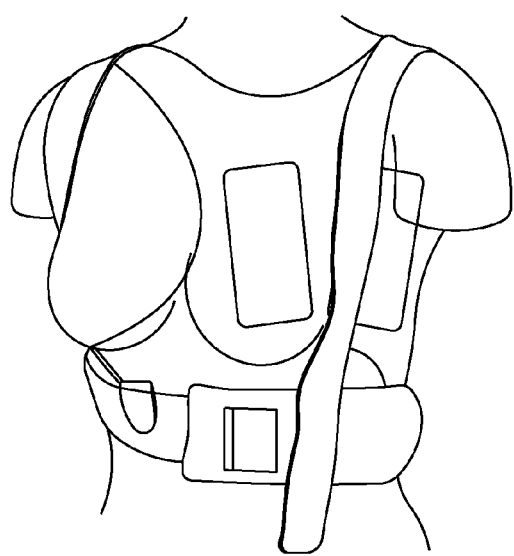
FIGS. 5A and 5B present front and back views, respectively, of shoulder straps in accordance with one or more embodiments.
Figure 5B:
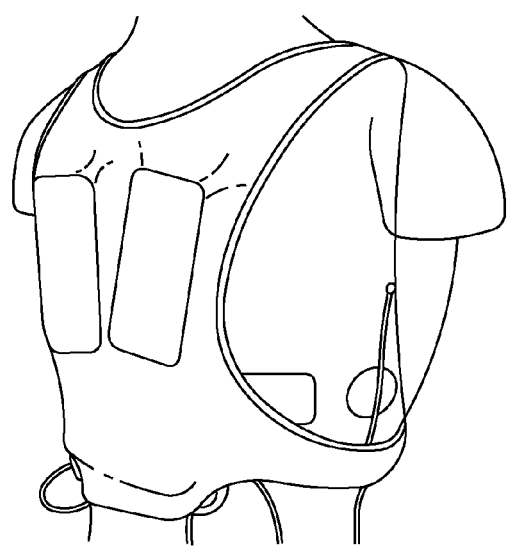

In accordance with one or more embodiments, a garment may function to keep electrodes in place against a patient's body while remaining comfortable during wear. Electrodes in the garment and electrode belt system provide vital functions. Sensing electrodes allow the system to monitor the patient's electrocardiogram (ECG) in order to assess the heart's activity. Therapy electrodes allow the system to deliver defibrillating energy in the event of a shockable rhythm, such as ventricular tachycardia or ventricular fibrillation. FIG. 1 presents a schematic of a patient-worn energy delivery apparatus, and FIGS. 2A and 2B present schematics (front and back views, respectively) of a defibrillator support garment housing components of the energy delivery apparatus in accordance with one or more embodiments.

In order to obtain a reliable ECG so that the monitor can function effectively and reliably, the sensing electrodes must be in the proper position and in good contact with the patient's skin. The electrodes need to remain in a certain position, and not move excessively or lift off the skin's surface. If there is movement or lifting, the ECG will be plagued with noise and can cause problems with the detection system and in the monitoring system. Similarly, in order to effectively deliver the defibrillating shock, the therapy electrodes must be in the proper position and in good contact with the patient's skin. If the therapy pads are not firmly positioned against the skin, there can be problems with high impedance, leading to a less effective shock. If the pads are not firmly positioned, there can also be damage to the patient's skin, such as burning, when the shock is delivered.

In accordance with one or more embodiments, any wearable medical diagnostic or treatment device may be used in conjunction with the disclosed support garments. In some nonlimiting embodiments, an energy delivery device may be supported. In one specific embodiment, the energy delivery device may be a defibrillator.

In accordance with one or more embodiments, a patient-worn energy delivery apparatus may include an electrode assembly as well as a wearable support garment for the assembly that surrounds the patient's chest and is worn against the skin. The apparatus may also include a monitor that the patient wears, such as around the waist or from a shoulder strap, which is an electronic device that monitors the patient and delivers defibrillating energy when necessary.

In accordance with one or more embodiments, a wearable cardioverter-defibrillator support garment may provide comfort and functionality under circumstances of human body dynamics, such as bending, twisting, rotation of the upper thorax, semi-reclining and lying down. These are also positions that a patient may assume if they were to become unconscious due to an arrhythmic episode. The design of the chest garment is generally such that it minimizes bulk, weight and undesired concentrations of force or pressure, while providing the necessary radial forces upon the sensing and energy delivery electrodes to ensure device functionality. The sensing electrodes may be distributed around the circumference of the chest garment and may be held against the patient's skin by these forces. Also held by these forces are various energy delivery electrodes, such as those which may be strategically positioned at a patient's front or back. Such electrodes may be centered on the patient, or oriented to a side of the patient's body.

A support garment for a patient-worn energy delivery apparatus may include a monitor-defibrillator disposed in a support holster. During wear, it is desired that a display unit be accessible at all times to the patient. A display unit that the patient uses to interact with the monitor-defibrillator may be provided and may, in some non-limiting embodiments, be carried in a pouch such as may be attachable to a band or belt incorporating a holster. Attachment may be made by fabric hook and pile fasteners, snaps, button, or by other various known techniques. In some embodiments, the entire outer surface of the garment, including the holster and the belt, may be made of a nylon pile, permitting the patient to attach the display wherever convenient. In an alternative embodiment, a pouch may be attached to a shoulder strap of the support garment which may be a preferred position, for example, during sleep. If desired, a thigh strap may be used to restrain the lower end of the monitor holster. The holster may include a pocket for retaining the monitor-defibrillator. The monitor-defibrillator may be held in the pocket by a flap.

A support garment may involve a chest garment having a back panel, side portions and back reinforcements. The side portions may extend laterally from either side of the lower back portion of the chest garment, and may be attachable to each other to define a belt or band for the chest garment. The band may generally be fitted around a patient's chest, such as under a patient's breasts, when the garment is worn. Preferably, the chest garment may be made of open-weave elasticized mesh fabric, such as that with bidirectional stretch. The fabric may be oriented, such as in a back panel and side portion extensions, so that the most aggressive stretch axis is placed horizontally with respect to the support garment and hence the patient. This orientation may ensure that maximum available inward force is applied to the electrode axis during wear, to enhance electrode function while minimizing fabric coverage on the patient's body, thereby enhancing comfort. Likewise, in the case of back reinforcements, the fabric may be oriented so that the most aggressive stretch axis is located diagonally to the chest garment, or along a long axis of the reinforcement, to optimize forces upon the rear energy delivery electrodes.

In some preferred embodiments, pockets housing energy delivery electrodes may be included, such as a rear energy delivery electrode pocket and a front energy delivery electrode pocket. The pockets may be made from a non-elastic mesh fabric designed to isolate the metallic energy delivery electrode surfaces from the skin of the patient while allowing a conductive gel that may be automatically extruded from the electrodes to easily pass through. This gel may be extruded from capsules within the electrode housings upon receipt of a signal from the monitor-defibrillator after declaration by the detection circuitry within the monitor-defibrillator of the occurrence of a treatable cardiac condition. The forces applied to the electrodes by the fabric, in addition to the use of the conductive gel, may help ensure that proper contact and electrical conductivity with the patient's body are maintained, even during body motions. Conventional fasteners, such as snaps or buttons, may close the pockets once the electrodes are inserted.

In accordance with one or more embodiments, unequal omnidirectional and bi-directional stretch of the fabrics may be implemented to apply the necessary forces onto the various electrodes in the harness, while the patient is in various body positions or during motions resulting from normal daily activities. These may allow the use of capacitive or other non-ionic sensing electrodes thereby enhancing patient comfort and adding significant noise immunity. These electrode types avoid the necessity of using adhesively attached electrodes, such as those used for short term monitoring during studies or monitoring in an intensive care facility. Electrodes requiring various skin preparing substances may be avoided. As the patient-worn energy delivery device is designed to be used by the patient for relatively long-term monitoring (up to six months), the non-adhesive and non-ionic electrodes may provide comfort and long life and may preclude the patient having to change electrodes after a short wear time.

In accordance with one or more embodiments, an electrode harness may contain a plurality of sensing electrodes, such as a driven ground electrode, at least one rear energy delivery electrode and at least one front energy delivery electrode. In some specific nonlimiting embodiments, two rear energy delivery electrodes are used. The harness may also contain a plurality of wiring conductors interconnecting the various electrodes to each other and to the monitor-defibrillator.

In accordance with one or more embodiments, areas surrounding the sensing electrode zones may be covered or coated with a high-friction elastomer which surrounds the electrode housings, to preclude movement relative to the skin, thus reducing or eliminating motion artifacts on the sensed signals obtained. In addition, capacitive or other non-ionic electrode elements may be used to further reduce motion artifacts. Furthermore, related system software may analyze signals obtained from the patient's skin to detect excessive noise. A low amplitude ac signal may be induced onto the patient's skin at the driven ground electrode site. This signal may be sensed by each sensing electrodes real-time. If the induced signal becomes erratic or nonexistent, the monitor-defibrillator may alert the patient, such as via a tactile vibrator contained within the driven ground electrode housing and an audible message emitted by a speaker in the patient display, that the sensing electrode contact within the skin is substandard and that the chest garment needs to be repositioned or adjusted.

In some embodiments, a chest garment may include an elasticized fabric force member attached to the inside of the garment with fabric loops. Conventional garment hook and eye fasteners may attach this member to the ends of the garment outer shell and the member may be varied in length at manufacture to impart the desired forces to the electrodes.

The garment may generally be constructed using tolerances that are considerably closer than those customarily used in the garment trades. The materials of construction are chosen for functionality, comfort and biocompatibility. The materials wick perspiration from the skin.

In some embodiments, adjustable length shoulder straps may be provided to allow compensation for varying torso lengths and to permit placement of the sensing electrode axis within the desired zone. The straps may also contribute to proper placement of the energy delivery electrodes and ensure that sufficient pressure is applied to the electrodes in the event of the need to deliver a defibrillation shock upon detection of a treatable arrhythmia. FIGS. 3A through 5B illustrate the shoulder strap design.

In accordance with one or more embodiments, shoulder straps may be attached in front of the patient's body rather than being routed under the patient's arms and attached in the back. In some embodiments, the shoulder straps may function similar to those of a backpack. Two shoulder straps may be generally anchored at and extend from the back of the garment and attach to the front of the garment. In some embodiments, a series of buttons around the garment, as well as a series of holes in the straps, may provide a range of adjustments to accommodate a variety of patient sizes and body shapes. In this way, the support garments can accommodate various body shapes and sizes, as well as both male and female patients. Some patients may be more comfortable wearing the straps towards the center, while other patients may be more comfortable wearing the straps outwards toward the sides. In either case, in an alternative embodiment, the straps may be permanently attached to the garment outer shell in a fixed position.

The shoulder straps may also be adjustable, such as using a slider assembly, fabricated from metal or plastic. Since both straps fasten to the front, the design helps to position the garment and the electrode belt attached to it, keeping the electrodes and therapy pads in the proper position on the patient's ribcage and in contact with the patient's skin. By keeping the electrodes in the proper position, the approach helps to reduce the incidence of improperly positioned electrodes and sliding electrodes. Patient comfort is improved because the shoulder straps do not go under arms and do not button in back. Use is also facilitated because a patient will not need to use a mirror to see the back. As a result, trial and error should be minimized. Soiling may also be deterred.

Figure 6:
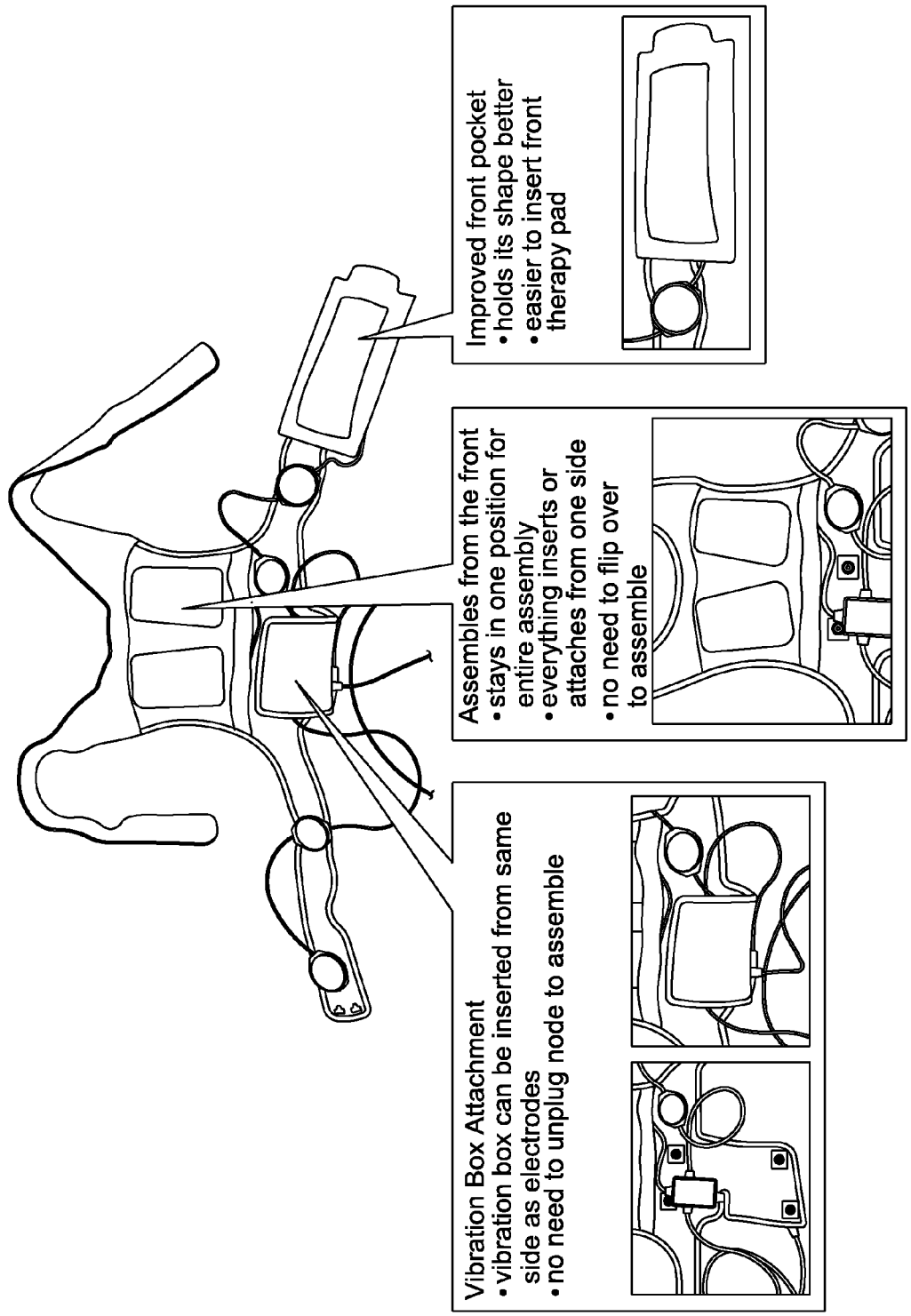
FIG. 6 presents a defibrillator support garment configured for one-sided assembly in accordance with one or more embodiments.

In accordance with one or more embodiments, overall design may simplify the garment assembly process. At least one embodiment is directed to a garment configured to allow assembly to be performed entirely from one side of the garment, without having to turn over the garment. FIG. 6 illustrates a garment configured for one-sided assembly. Conventional garments may require the electrode belt to be partially assembled from the outside of the garment and then the garment must be flipped over to complete the assembly process. One sided assembly may facilitate proper positioning of electrodes, as well as address patient concerns regarding complexity.

In accordance with one or more embodiments, one-sided assembly may take place on the inside of the garment which is against the patient's skin. The garment may have openings on the inside to facilitate assembly. For example, openings in the rear panel may facilitate insertion of therapy pads. A flap may replace a strap for securing the vibration box. The front therapy pad and ECG electrodes may also be attached from the same side of the garment. After assembly, the patient can change the shoulder strap length from the front, if necessary, to adjust the fit for improved performance and comfort.

The chest garment may generally be constructed to allow the patient to easily disassemble the electrode harness so it may be placed readily into a clean garment. Disassembly may involve releasing the conventional garment snap fasteners and disconnecting the sensing electrodes and the driven ground electrode from the garment body. The energy delivery electrodes may be removed from the chest garment by unfastening conventional garment snaps and removing the electrodes from their pockets. The electrode harness can then be removed from its position. Complex or unconventional mechanisms are thus avoided, and the patient may be trained rapidly in the assembly and use of the device. In accordance with one or more embodiments, assembly of the system is generally the reverse of disassembly.

Figure 7A:
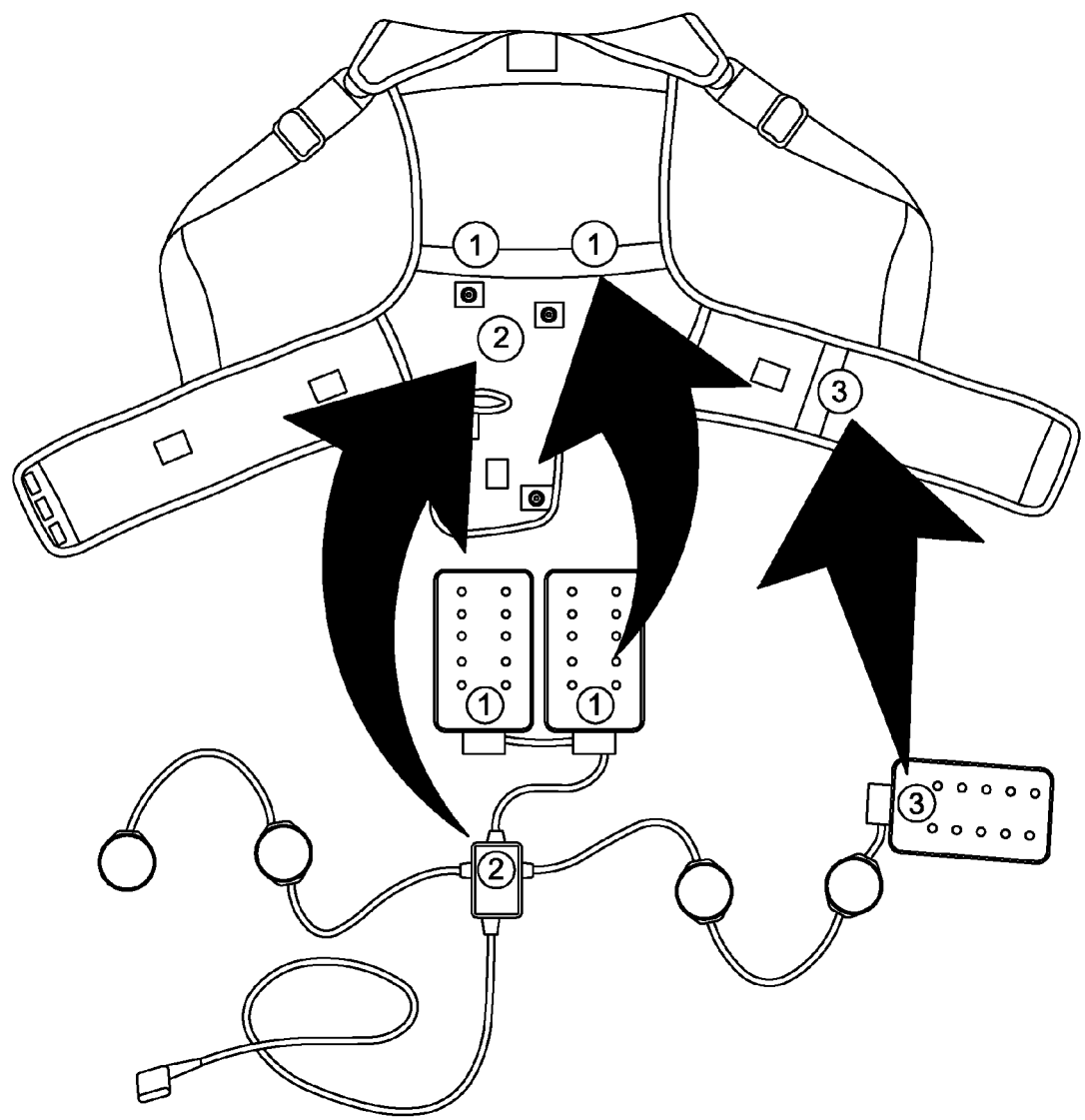
FIGS. 7A and 7B present schematics of coding systems to facilitate assembly in accordance with one or more embodiments.
Figure 7B:
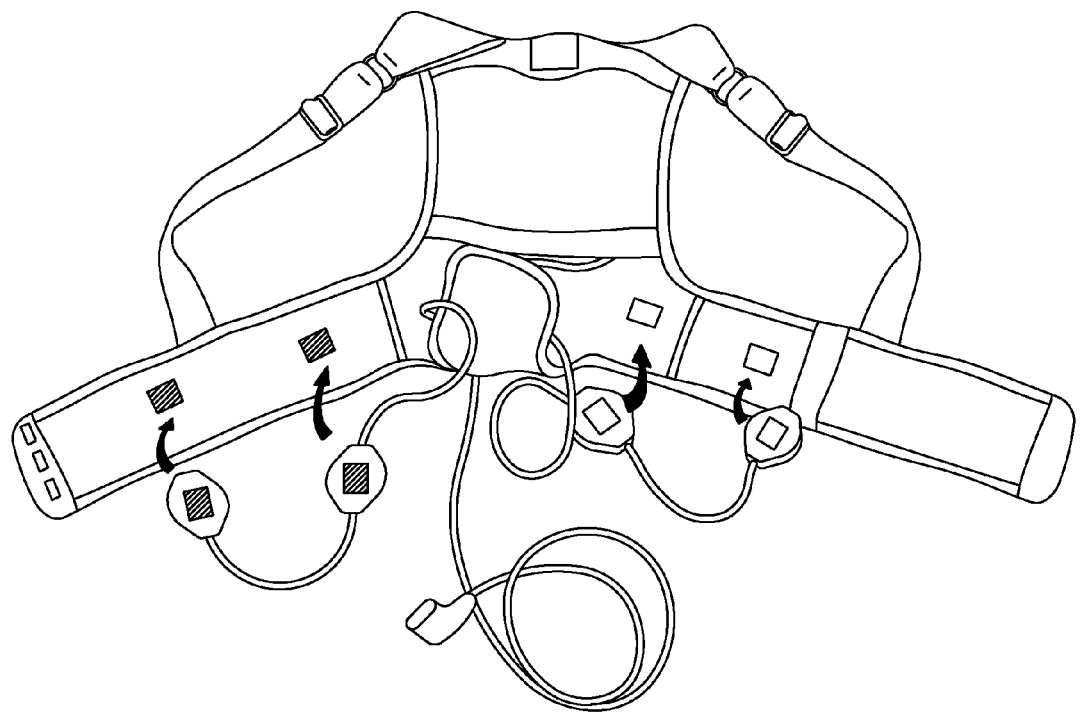

In accordance with one or more embodiments, components may be coded to simplify assembly. FIGS. 7A and 7B present schematics illustrating nonlimiting examples of coding systems that may be implemented. Various indicia, such as coloring or numbering, may be used to code components. For example, components of the electrode belt may be coded, and a corresponding code may be integrated on the garment. To assemble the electrode belt to the garment, a user may match components based on the code. In a similar fashion, some of the components can be color coded to help with the assembly process, and to assure that the components are assembled to the proper place. An example of a component that needs to be assembled into the proper place is the sensing electrodes on the electrode belt. To assemble the electrode belt to the garment, for example, a user may match the colors on the back of the sensing electrodes to the same colors on the garment. In some nonlimiting embodiments, different colors of hook-and-loop fastening fabric are used to facilitate the assembly.

In accordance with one or more embodiments, the elastic strap that wraps around the patient's chest may have a width selected to improve comfort. The width may generally be significantly wider than conventional chest straps. An elastic material, such as Nylon/Spandex, which is commonly used in undergarments, lingerie, and athletic apparel, can be used for the wide strap. The stretch rate of the wide strap allows it to accommodate a slightly wider range of chest circumferences while still improving patient comfort. The wider chest strap may prevent electrodes from flipping over and losing contact, which can be a significant problem with, for example, obese patients. The wider chest strap may provide even pressure to all of the electrodes, providing improved performance of the electrodes by minimizing electrode lift and sliding.

In accordance with one or more embodiments, a length of the band or belt may be adjusted by various known structures and methods. The practical range of adjustment of the belt length may vary. In some embodiments, the smallest circumference obtainable is virtually zero inches. Additionally, by utilizing an extension, the largest circumference obtainable can be extremely large.

In accordance with one or more embodiments, the entire garment may be made from a lightweight, breathable fabric. The shoulder straps may be made from the same materials as the rest of the garment, so there is no need for heavy padding. The material is flexible, with elastic edging for comfort and freedom of movement. Because of the low spring rate of the material, the number of sizes to accommodate a wide range of patients may be reduced.

Figure 8A:
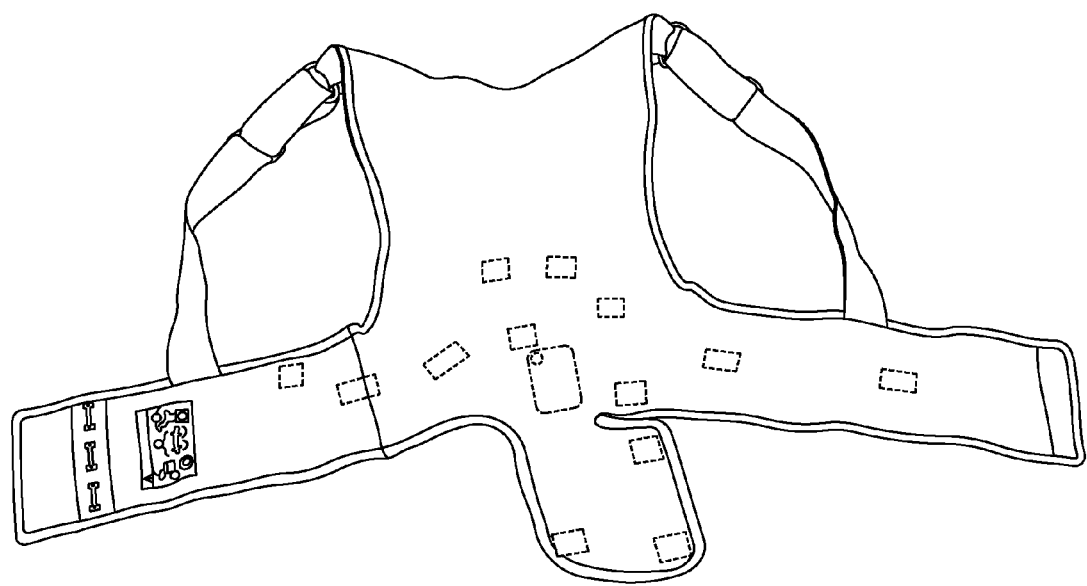
FIGS. 8A and 8B present front and back views of a support garment in accordance with one or more embodiments.
Figure 8B:
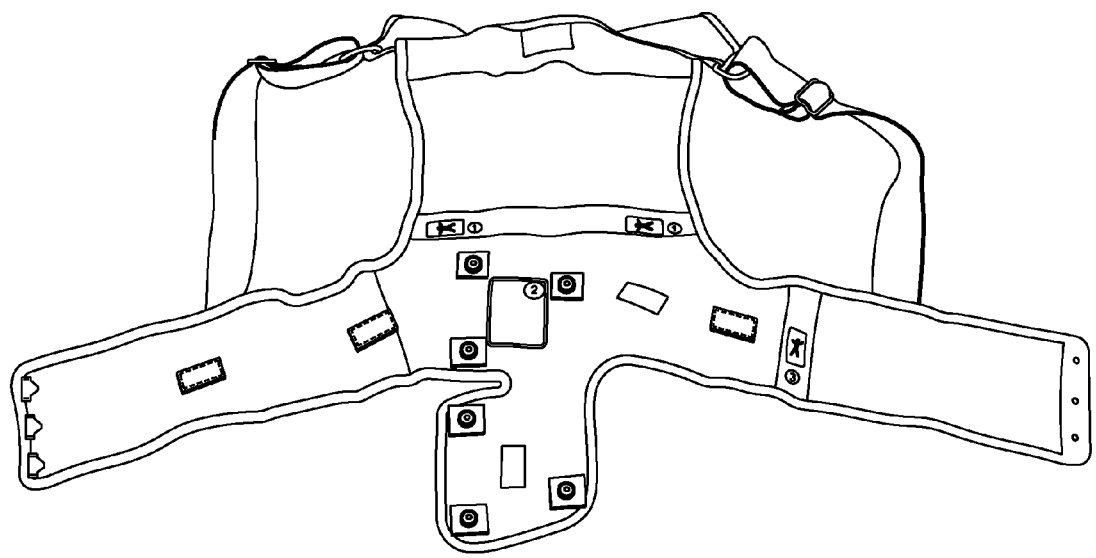

In accordance with one or more embodiments, a support garment may be constructed and arranged to facilitate one-sided assembly of the garment by a patient as opposed to conventional garments which require assembly work to be done on both sides. FIG. 8A illustrates the outside of a garment and FIG. 8B illustrates inside of the garment. As illustrated, the outside is substantially free of component attachment points which are instead all located on the inside of the garment. Beneficially, the cleaner exposed back panel in comparison to conventional garments may prevent components or wiring to catch or otherwise become undone by accident. The garments may generally be more lightweight and feel less constrictive than conventional support garments. The material of the garment may generally rebound. In some nonlimiting embodiments, the garment may be made of a material including about 85% spandex and 15% nylon. The elasticity and spring rate of the material may reduce the number of sizes need to properly fit a diverse patient group. In some nonlimiting embodiments, five garment sizes may accommodate a majority of the patient pool. The garments may be associated with a performance increase in terms of patient compliance as well as less noise in the sensing electrodes due to improved fit. Patient compliance may lead to more frequent laundering of the garments as recommended to prevent the garments from becoming stretched out with wear. In addition to the various electrodes, the tension against the patient's skin provided by the garment may facilitate maintaining the proper positioning of other associated components, such as a vibrating tactile alarm or an accelerometer. The material and fit of the support garment may generally help provide better baseline readings.

Figure 9A:
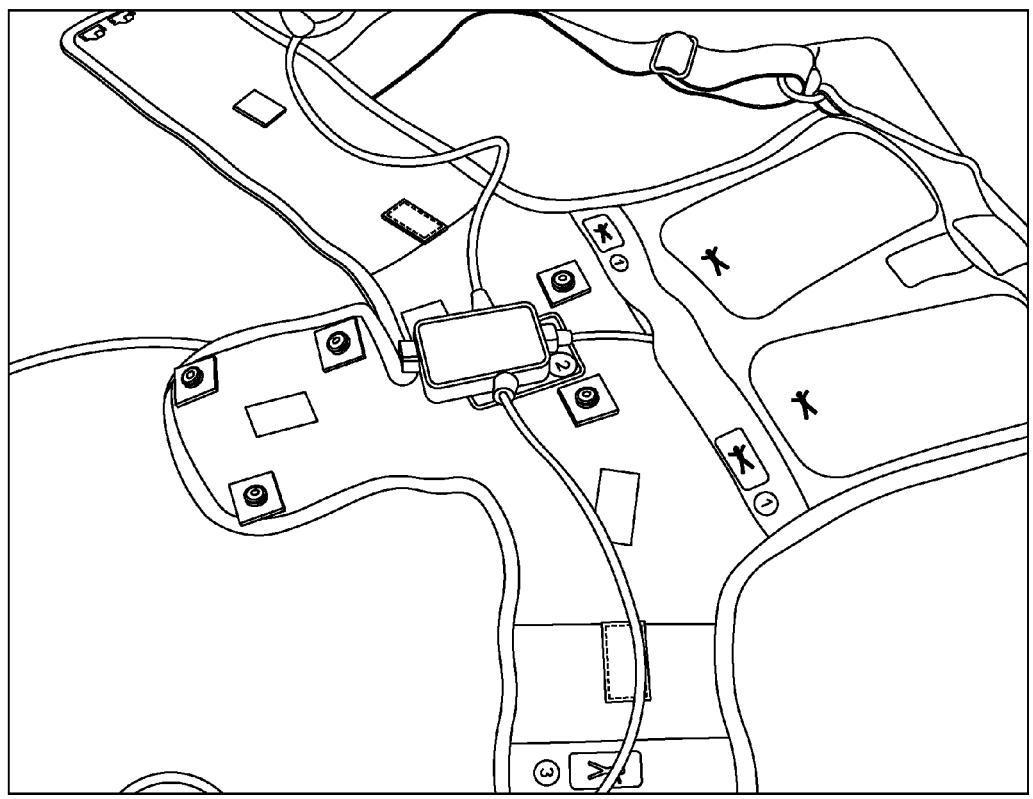
FIGS. 9A and 9B present views illustrating one-sided assembly of a support garment in accordance with one or more embodiments.
Figure 9B:
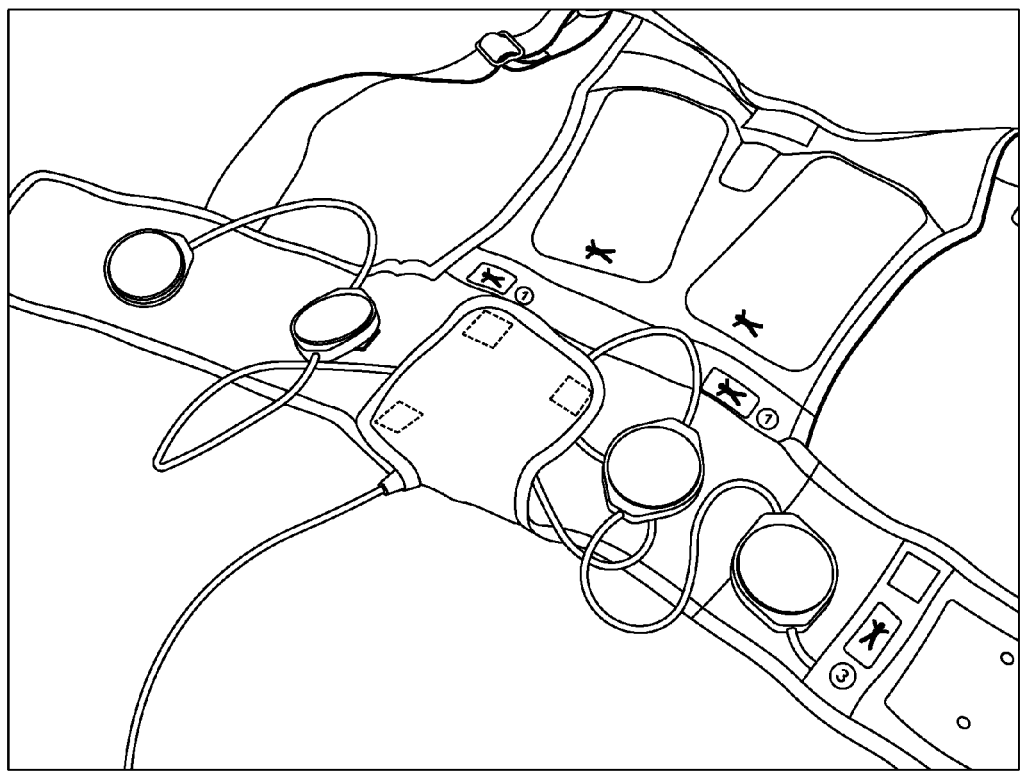

During assembly, therapy pads may be inserted and fastened into their respective pockets on the inside of the garment as illustrated in FIG. 9A. The junction box and sensing electrodes may then be secured in place in the inside of the garment as illustrated in FIG. 9B. In some embodiments, a coding system, for example based on coloring, icons or numbering, may be used to facilitate assembly. The patient may then put on the assembled garment and secure it for wear. As illustrated in FIG. 9B, the garment when assembled may define a notch or cutout to facilitate wiring from the junction box to the defibrillator or monitor. The shoulder straps may be positioned so as to be worn more to the front of a patient rather than under the arm as in conventional garments. A wider chest band may facilitate holding detection and therapy electrodes in proper position, as well as preventing undesirable roll-over of the band. In some embodiments, a label may be imprinted on the garment rather than attached.

To accommodate a wide range of sizes of patients, defibrillator support garments are offered in various sizes. This is similar to the consumer size designators S, M, L, and XL commonly used when purchasing T-shirts and other clothing. With the wearable defibrillator system, typically as part of the fitting and training process, patients are measured for the size garment they need to wear. To measure patients, typically a fitter tells the patient to stand up and remove all upper body clothing. A measuring tape is then placed around the patient's chest, centered at the xiphoid, to measure the patient's circumference in inches or centimeters. The fitter then uses a chart to determine the proper size garment from the chest measurement. For example, if the patient measures 40 inches in circumference, the patient should receive a corresponding size garment. There are a number of problems with the existing method of measuring patients. The current method requires that the fitter has a measuring tape. Further, the fitter must be able to properly read the tape in inches or centimeters. If the fitter uses the same measuring tape from one patient to another, and since the tape is in contact with the patient's body, the tape can become soiled after multiple uses. In extreme cases, this method can lead to fitters not measuring patients, resorting to guessing or estimating the patient's size. This can lead to fitting the patient with the wrong size garment, which can lead to comfort issues, and degraded device performance.

Figure 10A:
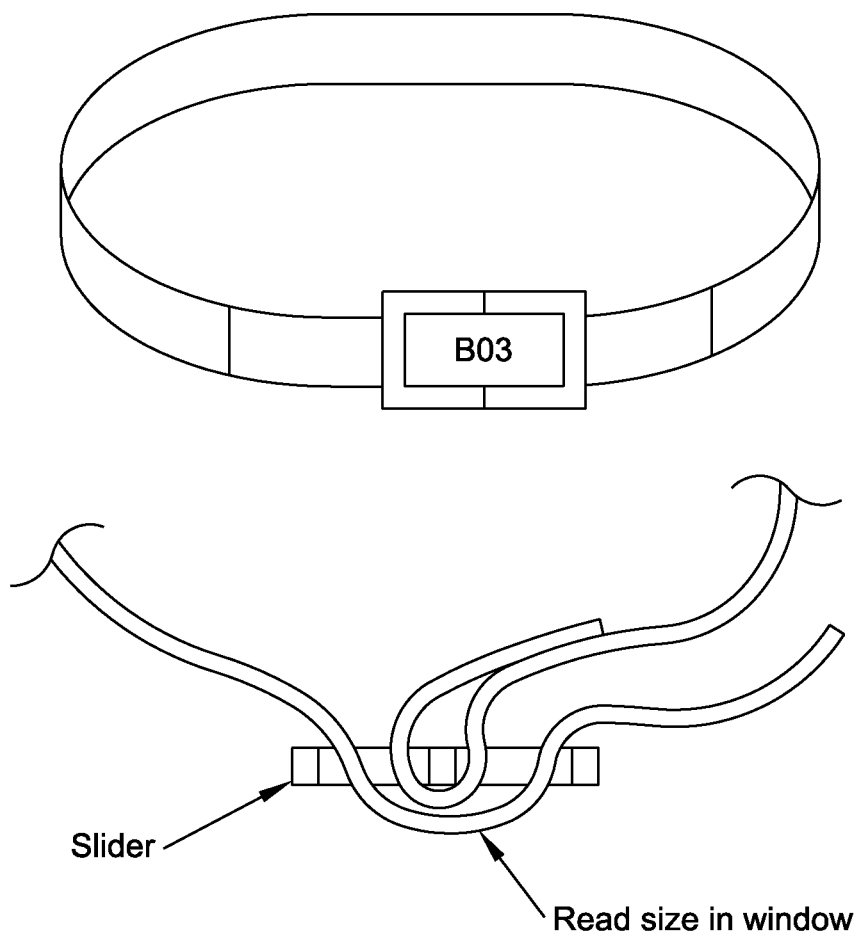
FIGS. 10A and 10B present schematics relating to a garment sizing technique in accordance with one or more embodiments.
Figure 10B:
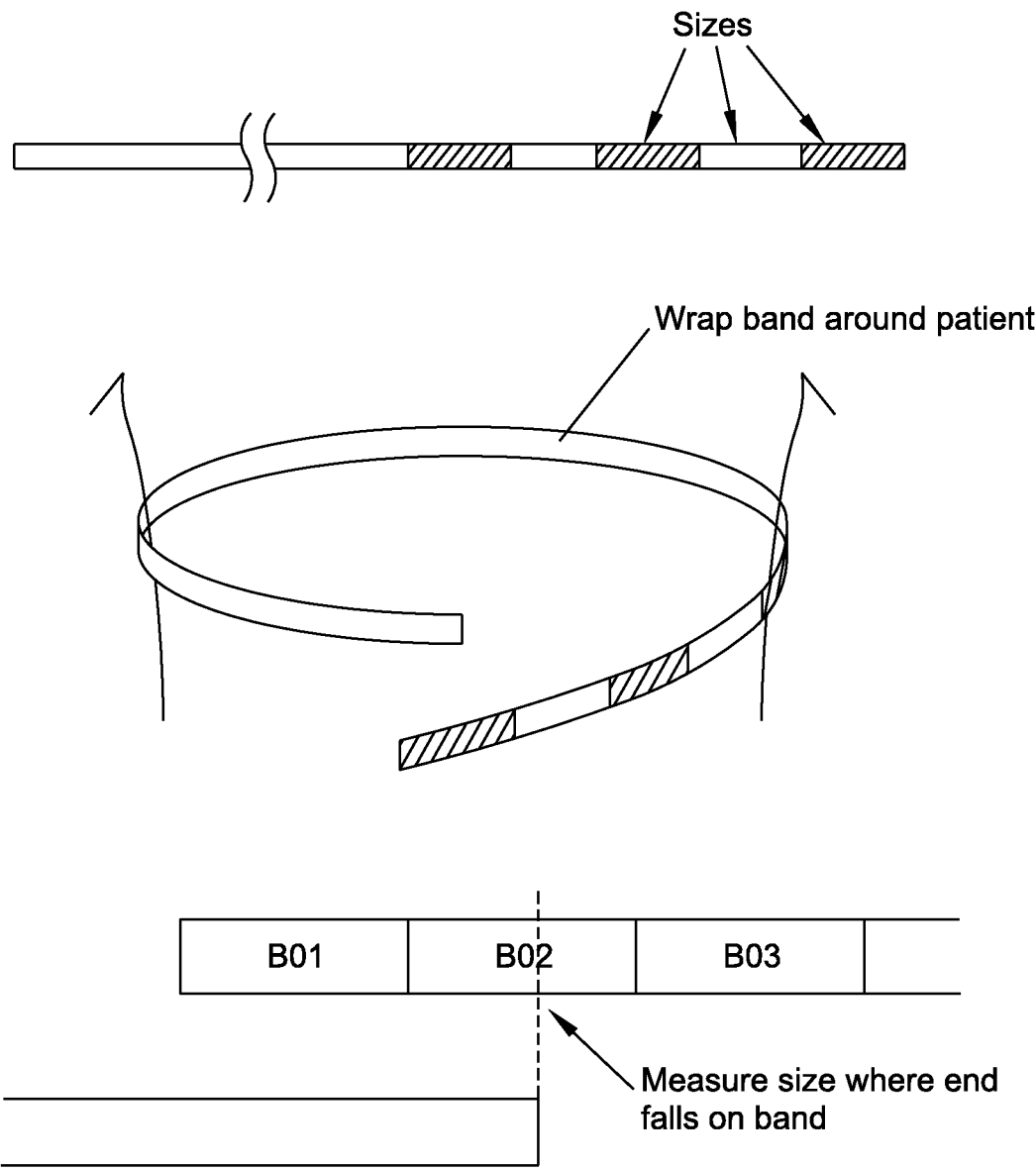

In accordance with one or more embodiments, a patient measuring band may be used to properly size the garment. FIGS. 10A and 10B illustrate this technique. The design of the measuring band may resemble that of a tape measure. Indicia other than standard numbers, however, may be used to indicate what size garment to use. In some embodiments, areas or zones along a length of the measuring band may indicate what size garment to use. In some nonlimiting embodiments, five sizes may be used to accommodate a wide range of patients, for example, each proportioned to fit a segment of patients' chest circumference. The various sizes may be dimensioned so that the proper electrode spacing is implemented and maintained. The inter-zone distance, which is the distance between the sensing electrodes, each other and the driven ground electrode, may be proportional to the circumference the garment is to fit. For example, if there are five garment sizes, there may be five "blocks" of measurements corresponding with the body circumference that these sizes are to be used. The blocks may designate or correspond to the garment size. The patient measuring band may be made of a non-stretchable, low-cost material, such as vinyl or a tear resistant paper. It may typically be fashioned out of a strip of material large enough to measure around the patient. It may be a disposable product, used once and thrown away, avoiding cross contamination.

In some embodiments, the size blocks may be color coded to further help identify the garment size. As an alternative, symbols, icons, or colors only, can be used instead of alphanumeric designators to indicate the garment size. The measuring band can be printed as a double-sided unit, so it would not matter which direction the band was wrapped around the patient's body. As an alternative, the invention can be designed with a window that allows the garment size to show through. It would be wrapped around the patient's body similar to a belt, with the garment size showing in a window similar to a belt buckle in the front of the unit.

Precise fitting, within a garment size, may be accomplished by an end section extended and attached to the garment outer shell. The end sections may be provided in any desired increment, such as one inch increments, to the fitter for fine adjustment to the chest circumference. The end sections may be attached to the chest garment with a standard fastener. A fastener tab may be removed once the appropriate end section length is determined and installed. This precludes further adjustment by the patient. In the event of a patient having a significant weight gain or loss, the fitter, at the patient's periodic checkup, may replace the end section with one sized more appropriately to the patient's current measurements.

In accordance with one or more embodiments, disclosed garments may provide better performance, more comfort, and improved compliance in comparison to conventional garments. The design may simplify the assembly process for patients and the people responsible for fitting and training patients. The design may also improve compliance with garment changing, which could lead to improved performance and comfort by encouraging more frequent changing and laundering of the garment.

Having now described some illustrative embodiments, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives.

It is to be appreciated that embodiments of the devices, systems and methods discussed herein are not limited in application to the details of construction and the arrangement of components set forth in the following description or illustrated in the accompanying drawings. The devices, systems and methods are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Those skilled in the art should appreciate that the parameters and configurations described herein are exemplary and that actual parameters and/or configurations will depend on the specific application in which the systems and techniques of the invention are used. Those skilled in the art should also recognize or be able to ascertain, using no more than routine experimentation, equivalents to the specific embodiments of the invention. It is therefore to be understood that the embodiments described herein are presented by way of example only and that, within the scope of the appended claims and equivalents thereto; the invention may be practiced otherwise than as specifically described.

Moreover, it should also be appreciated that the invention is directed to each feature, system, subsystem, or technique described herein and any combination of two or more features, systems, subsystems, or techniques described herein and any combination of two or more features, systems, subsystems, and/or methods, if such features, systems, subsystems, and techniques are not mutually inconsistent, is considered to be within the scope of the invention as embodied in the claims. Further, acts, elements, and features discussed only in connection with one embodiment are not intended to be excluded from a similar role in other embodiments.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A patient-worn energy delivery system, comprising:
   a defibrillator including:
      a plurality of sensing electrodes configured to sense a cardiac function of a patient;
      at least two therapy electrodes configured to provide a therapeutic shock to the patient; and
      a junction box comprising circuitry coupled to the plurality of sensing electrodes and the at least two therapy electrodes;
   a support garment constructed and arranged to support the defibrillator,
      the support garment made from a fabric having an outside surface and an inside surface,
      the support garment configured to be worn about a chest of the patient and constructed and arranged to allow for one-sided assembly of the plurality of sensing electrodes, the at least two therapy electrodes, and the junction box, wherein the plurality of sensing electrodes, the at least two therapy electrodes, and the junction box are configured to be assembled along the inside surface of the fabric of the support garment without having to flip over the support garment during assembly, and wherein the plurality of sensing electrodes are further configured to be directly and removably attached to the inside surface of the fabric of the support garment,
      the support garment comprising a back portion, a belt defined by side portions extending from the back portion, and adjustable shoulder straps configured to be selectively attached to the belt,
      the support garment further comprising a flap and one or more fasteners along the inside surface of the support garment, the flaps and fasteners for securing the junction box to the support garment while the patient is wearing the garment; and
   a coding system configured to facilitate releasable attachment of the plurality of sensing electrodes, the at least two therapy electrodes, and the junction box along the inside surface of the fabric of the support garment,
   wherein the coding system comprises one or more codes on the plurality of sensing electrodes, the at least two therapy electrodes, and the junction box, and one or more corresponding codes on the support garment to indicate to the patient the appropriate corresponding locations on the support garment for assembling the plurality of sensing electrodes, the at least two therapy electrodes, and the junction box during the one-sided assembly.

2. The system of claim 1, wherein the shoulder straps are configured to be selectively attached to the belt at a front of the patient.

3. The system of claim 1, wherein the fabric of the support garment comprises an elastic, low spring rate material.

4. The system of claim 3, wherein the material comprises about 85% spandex and about 15% nylon.

5. The system of claim 1, further comprising one or more of a patient display, a tactile alarm, and an accelerometer associated with the defibrillator.

6. The system of claim 1, further comprising at least one pocket configured to receive the at least two therapy electrodes at a front or back of the patient.

7. The system of claim 6, wherein the at least one pocket is constructed and arranged to isolate a metallic surface of the at least two therapy electrodes from skin of the patient while allowing a conductive gel associated with the at least two therapy electrodes to pass through.

8. The system of claim 1, wherein the support garment is constructed and arranged to distribute the plurality of sensing electrodes around a circumference of the chest of the patient.

9. The system of claim 8, wherein the fabric of the support garment includes at least one zone coated with a high-friction elastomer to deter movement of the sensing electrodes relative to skin of the patient.

10. The system of claim 8, wherein at least one of the plurality of sensing electrodes is non-ionic or non-adhesive.

11. The system of claim 1, wherein the outside surface of the fabric of the support garment is substantially free of attachment points relating to components of the defibrillator.

12. The system of claim 1, wherein the support garment defines a notch or a cutout to facilitate wiring from the junction box upon assembly.

13. The system of claim 1, wherein the support garment is constructed and arranged to provide uniform pressure to one or more electrodes associated with the defibrillator.

14. The system of claim 1, wherein the support garment is sized to promote proper spacing between electrodes associated with the defibrillator.

15. The system of claim 1, wherein the coding system involves color matching between the plurality of sensing electrodes and the support garment.

16. The system of claim 1, wherein the support garment further comprises an extension to facilitate adjustment of a circumference of the support garment.

17. The system of claim 1, further comprising an elasticized fabric force member attached to the inside surface of the fabric of the support garment.

18. The system of claim 1, wherein the support garment includes at least one hook and pile fastener, snap, or button for direct attachment of the plurality of sensing electrodes to the inside surface of the fabric of the support garment.

19. The system of claim 18, wherein the coding system involves color matching between the plurality of sensing electrodes and the least one hook and pile fastener, snap, or button for releasable attachment of the plurality of sensing electrodes directly to the inside surface of the fabric of the support garment.

20. The system of claim 18, wherein the plurality of sensing electrodes are configured to be directly attached by hook-and-loop fasteners to the inside surface of the fabric of the support garment.

21. The system of claim 1, wherein the coding system involves number matching between the plurality of sensing electrodes and the support garment.

22. A patient-worn energy delivery system, comprising:
 a defibrillator including:
  a plurality of sensing electrodes configured to sense a cardiac function of a patient;
  at least two therapy electrodes configured to provide a therapeutic shock to the patient; and
  a junction box comprising circuitry coupled to the plurality of sensing electrodes and the at least two therapy electrodes;
 a support garment constructed and arranged to support the defibrillator,
  the support garment made from a fabric having an outside surface and an inside surface,
  the support garment configured to be worn about a chest of the patient and constructed and arranged to allow for releasable attachment of the plurality of sensing electrodes, the at least two therapy electrodes, and the junction box to the inside surface of the fabric of the support garment via one-sided assembly without having to turn over the support garment, wherein the plurality of sensing electrodes, the at least two therapy electrodes, and the junction box are configured to be assembled along the inside surface of the fabric of the support garment via the one-sided assembly,
  the support garment comprising a back portion, a belt defined by side portions extending from the back portion, and adjustable shoulder straps configured to be selectively attached to the belt,
  the support garment further comprising a flap and one or more fasteners along the inside surface of the support garment, the flaps and fasteners for securing the junction box to the support garment while the patient is wearing the garment; and
 a coding system configured to facilitate the releasable attachment of the plurality of sensing electrodes, the at least two therapy electrodes, and the junction box along the inside surface of the fabric of the support garment, the plurality of sensing electrodes further configured to be directly and removably attached to the inside surface of the fabric of the support garment,
 wherein the coding system comprises one or more codes on the plurality of sensing electrodes, the at least two therapy electrodes, and the junction box, and one or more corresponding codes on the support garment to indicate to the patient the appropriate corresponding locations on the support garment for assembling the plurality of sensing electrodes, the at least two therapy electrodes, and the junction box during the one-sided assembly.

23. The system of claim 22, wherein the coding system involves color matching between the plurality of sensing electrodes and the support garment.

24. The system of claim 22, wherein the support garment includes at least one opening in the back portion to facilitate insertion of the at least two therapy electrodes.

25. The system of claim 22, wherein the support garment includes at least one hook and pile fastener, snap, or button for direct attachment of plurality of sensing electrodes to the inside surface of the fabric of the support garment.

26. The system of claim 25, wherein the plurality of sensing electrodes are configured to be directly attached by hook-and-loop fasteners to the inside surface of the fabric of the support garment.

* * * * *